United States Patent [19]

Idriss

[11] Patent Number: 5,176,641

[45] Date of Patent: Jan. 5, 1993

[54] IMPLANTABLE DRUG INFUSION RESERVIOR HAVING FLUID IMPELLING RESILIENT FOAM MEMBER

[75] Inventor: Samir F. Idriss, Hyde Park, Mass.

[73] Assignee: Infusaid, Inc., Norwood, Mass.

[21] Appl. No.: 726,659

[22] Filed: Jul. 8, 1991

[51] Int. Cl.⁵ ............................................ A61M 37/00
[52] U.S. Cl. .................................... 604/133; 604/131
[58] Field of Search ..................... 604/133, 131, 892.1, 604/93

[56] References Cited

U.S. PATENT DOCUMENTS

| | | | |
|---|---|---|---|
| 3,871,377 | 3/1975 | Treace | 604/133 |
| 4,539,004 | 9/1985 | Eckenhoff et al. | 604/131 |
| 4,661,093 | 4/1987 | Beck et al. | 604/133 X |
| 4,668,231 | 5/1987 | de Vries et al. | 604/891.1 |
| 4,687,468 | 8/1987 | Gianturco | 604/153 |
| 4,772,263 | 9/1988 | Dorman et al. | 604/132 |
| 4,813,951 | 3/1989 | Cannon | 604/891.1 |

FOREIGN PATENT DOCUMENTS

| | | | |
|---|---|---|---|
| 0295504 | 12/1988 | European Pat. Off. | 604/131 |
| 0344895 | 12/1989 | European Pat. Off. | 604/131 |
| 8910157 | 11/1989 | World Int. Prop. O. | 604/131 |

Primary Examiner—John J. Wilson
Assistant Examiner—Jeffrey A. Smith
Attorney, Agent, or Firm—Sughrue, Mion, Zinn, Macpeak & Seas

[57] ABSTRACT

An implantable infusion reservior having a resilient foam member in a rigid housing to urge fluid to an implantation site. The foam member compresses upon charging and then expands to maintain a predetermined pressure characteristic within the fluid. The foam replaces the previously used two-phase propellant and eliminates the need for a hermetic metal bellows. The foam may be either closed celled or open celled, with or without a barrier skin. The device can be conformal to any desired shape and employ various metering techniques to deliver accurate quantities of fluid.

19 Claims, 3 Drawing Sheets

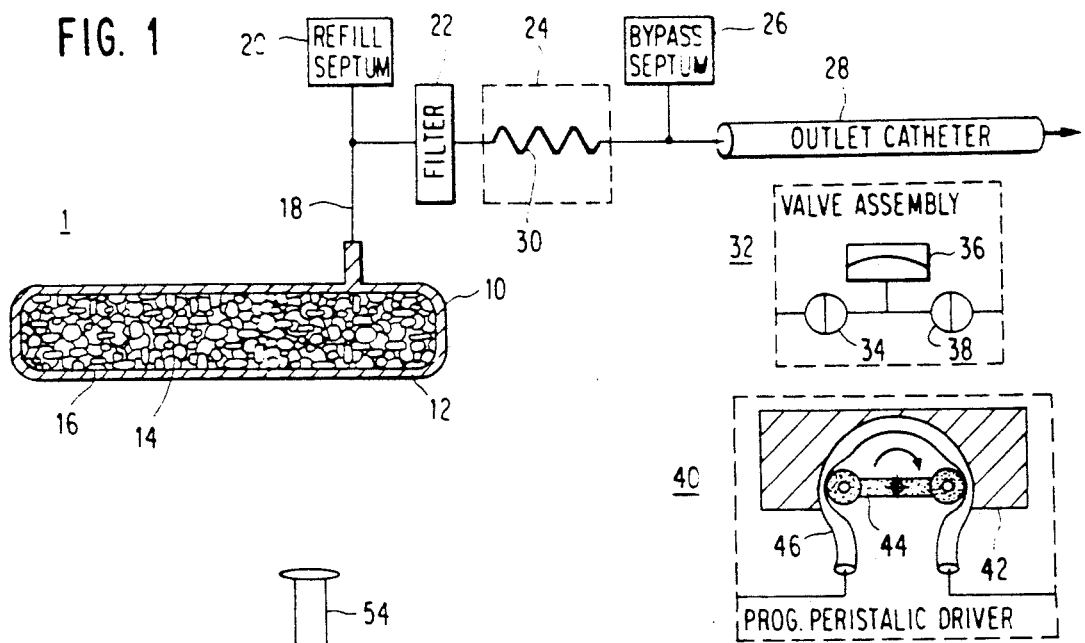
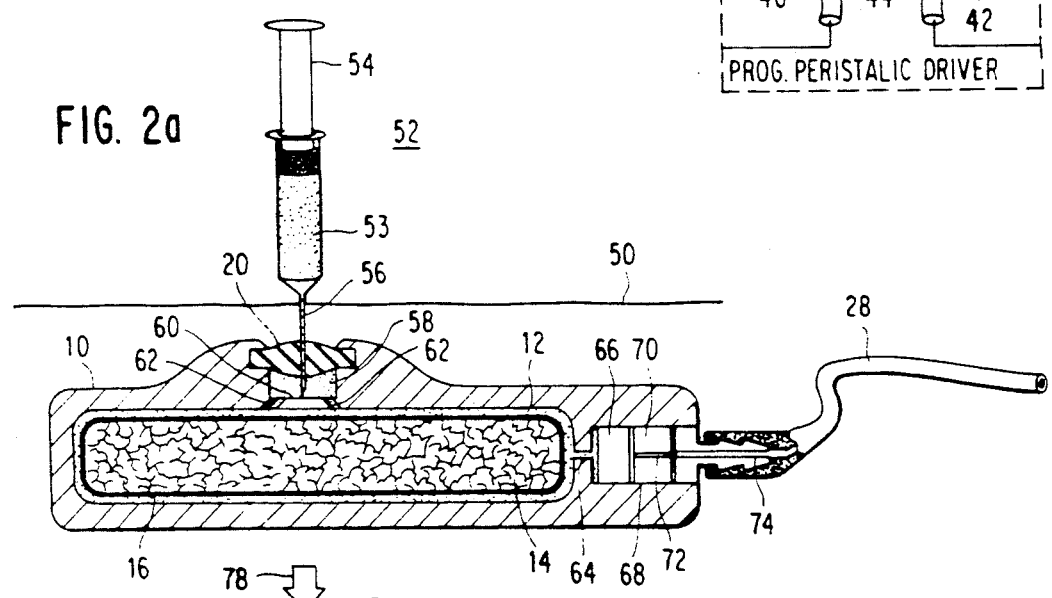
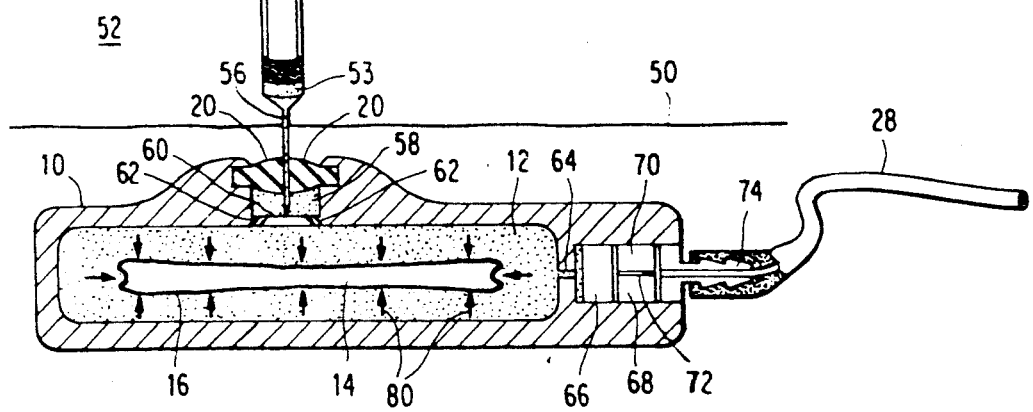

IMPLANTABLE DRUG INFUSION RESERVIOR HAVING FLUID IMPELLING RESILIENT FOAM MEMBER

BACKGROUND OF THE INVENTION

This invention relates to an implantable positive pressure infusion reservoir. In particular, it relates to an implantable drug infusion reservoir that eliminates the requirement for a bellows and two-phase propellent used as a primary drug storage reservoir.

Implantable drug infusion systems are commercially available. Typical are the Infusaid Model 100 and 400 pump systems. Those systems are based on the technology disclosed in U.S. Pat. No. 3,731,681 which employs a bellows, typically made of titanium for purposes of drug compatibility, as the main drug storage reservoir. Titanium has been chosen in the prior art additionally for its biocompatibility and its hermeticity when welded to other components of the pump. Moreover, systems in use today predicated on the technology of the '681 patent typically use Freon (DuPont trademark) as a two-phase constant pressure media for purposes of providing a delivery pressure tending to bias the bellows in a compressed position.

While such systems have become commercially viable, they are relatively expensive. For example, the titanium bellows per se typically costs between $100–$200. This is the piece part cost and does not include the costs associated with welding. Freon backfill and the like. Thus, the use of a bellows/Freon system and its corresponding material requirements are a major contributing factor in the cost of an implantable drug infusion system.

Additionally, the use of a bellows configuration carries with it inherent size and shape limitations and becomes less volume efficient for bellows having small diameters, long strokes and low spring rate pressures. To date, however, the use of the bellows configuration is the only major commercially viable system.

Other techniques have been proposed in the art such as U.S. Pat. No. 3,840,009. This reservoir concept employs a heat-sealed metallized film bag for containment of a two-phase charging fluid. The bag is then immersed in the drug solution and acts as a compliant reservoir as well as a motive pressure force. In such a system then, the use of the two-phase fluid is also required with the propellent media housed in a flexible member inside a larger volume reservoir.

Such a configuration, while eliminating the bellows may still be expensive to manufacture since environmental concerns have decreased the availability and raised the cost to purchase and store chlorofluorocarbons of the type used for implantable propellents.

Thus, there exists within the technology dealing with implantable drug infusion systems the need for a lower cost reservoir which utilizes less parts yet does not decrease the volumetric efficiency of traditional bellows devices. Moreover, such a system must be compatible with the stringent requirements of implantation into a living body together with drug compatibility over a range of drugs to be infused.

SUMMARY OF THE INVENTION

Given the shortcomings in the prior art, it is an object of this invention to provide an implantable drug infusion reservoir which significantly reduces costs, uses a minimum number of parts and is easier to manufacture than prior art systems, yet maintains volumetric efficiency.

Yet another object of this invention is to provide for an implantable drug infusion reservoir that is conformal in shape to a number of different implantation volumes, yet performs with a relatively constant fluid pressure.

These and other objects of this invention are fulfilled by the use of a flexible foam member which acts both as the drug storage reservoir and the pressure motive force to dispel the drug from the reservoir. The foam core replaces the bellows and the Freon charging fluid. Thus, when compared with the existing technology, the use of the foam member significantly reduces not only the cost of parts, but also the cost of manufacture and assembly. In addition, the foam member is generally conformal in shape to the complete interior of the drug storage area, improving volumetric efficiency. While circular or disk members are most common, the foam can be any shape.

The foam itself is sealed so that it will be impermeable to the drug and any gases dissolved in the drug solution. Thus, the foam member may be a closed cell foam or, a closed cell foam having a skin, coating or film. An open cell foam may also be used provided with a skin, coating or film. An open cell foam may also be sealed in a bag or isolated by a flexible diaphragm to provide the necessary impermeability. By utilizing the resilient foam member, the bellows, Freon and a Freon fill tube are eliminated from the drug infusion system. Additionally, the drug reservoir need no longer be hermetic to or compatible with Freon gas. Thus, alternative materials to titanium may be selected. The use of the foam member has an added advantage in that it allows other inert materials to be used as the basic reservoir housing, for instance, low cost plastics.

Moreover, the top cover for the housing which is typically a solid piece containing the septum, filter and needle stop can also be manufactured from materials other than titanium because weld compatibility is no longer required. Complex machining of titanium can be replaced by low-cost plastics injection molding. This is a secondary but significant advantage of utilizing a resilient foam reservoir.

Another advantage in the use of the foam member is that the foam itself deflects uniformly (in all directions) under hydrostatic pressure. The foam can therefore be manufactured in any shape to fill any heretofore wasted voids or spaces inside the housing; the single axis of travel required by the bellows is no longer a design limitation.

In operation, the implantable pump is manufactured with the foam in compression and sealed. By this technique the reservoir is pre-set to a minimum operating pressure condition. A syringe is inserted through the fill septum and pressure applied to dispense its contents. When the hydrostatic pressure of the fluid filling the reservoir reaches the initial compression pressure of the foam, the foam will deflect inwardly on all surfaces and the pump will begin to fill by compression of the foam. The deflection of the foam continues until the syringe is completely emptied or the back-pressure exhibited by the foam equals the hydrostatic pressure of the syringe. The syringe needle is then retracted from the inlet septum and the pump is ready for use. As drug is expelled from the reservoir to the outlet catheter, the foam gradually returns to its initial state and is thus automatically reset for subsequent refill.

This invention will be described in greater detail by referring to the attached drawing and the description of the preferred embodiments which follow.

BRIEF DESCRIPTION OF THE DRAWING

FIG. 1 is a schematic representation of an implantable drug infusion system utilizing the foam reservoir with different metering techniques;

FIGS. 2a and 2b are sequential cross-sectional operational views showing a different infusion system during reservoir refill;

DESCRIPTION OF THE PREFERRED EMBODIMENTS

Figure 3A:
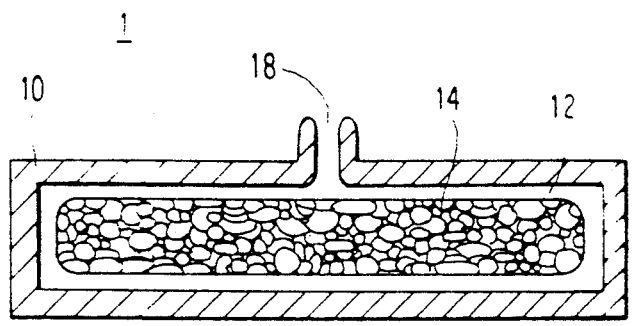
FIGS. 3a, 3b, 3c, 3d and 3e are cut away cross-sections illustrating various preferred embodiments within the scope of the invention.

Referring now to FIG. 1, a schematic view of the invention is depicted in use in an implantable infusion system. The implantable reservoir 1 contains a rigid housing 10 forming a sealed compartment containing a drug chamber 12. Within the chamber 12 is inserted a resilient foam member 14 to be described in detail herein. As illustrated in FIG. 1, the foam member 14 is conformal, that is it is cut, cast, or molded so that it occupies substantially the entire volume of the drug chamber 12. An inlet/outlet conduit 18 is located within the housing 10 to provide fluid communication with the drug chamber 12.

Attached to the conduit 18 are basic implantable infusion system elements consisting of refill septum 20, bacteria filter 22, flow metering device 24 (shown by dashed lines and to be described in detail herein), auxilliary bypass septum 26 and outlet catheter 28. These components are well established in the art and are shown only for purposes of illustration of a typical use of the invention. For instance, flow metering device 24 can be a flow restricting capillary 30 (shown attached to the system). It may also be an electronically controlled valve/accumulator/valve assembly 32, consisting of inlet valve 34, pressurized volume accumulator 36 and outlet valve 38. The flow metering component can also be a programmable peristaltic driver 40, consisting of rigid housing 42, rotating pinch roller 44 and peristaltic flow tubing 46. Each of these metering components is well known in the art and practiced commercially within the context of implantable drug infusion systems. The system could also be constructed without auxilliary bypass septum 26 or fashioned for one-time use by eliminating refill septum 20. All of these variations can be freely practiced with the invention herein described.

Comparing the device of FIG. 1 with a prior art drug infusion system, (e.g. U.S. Pat. No. 3,731,681) it is appreciated that by this invention the prior art bellows is eliminated. As such, the cost of manufacture is significantly reduced because the foam member 14 utilizes inexpensive processes of manufacture and assembly. Additionally, the available volume in the drug chamber 12 is maintained or increased since any dead volume associated with sliding clearance and nesting of the bellows is eliminated. The foam member eliminates the requirement for a separate charging fluid chamber as in prior art systems. That is, given the resiliency of the foam member 14, the requirement in the prior art for a separate system or device to provide a compressive force on the bellows is not present. In addition to eliminating the volumetric requirement of the charging fluid chamber, other advantages occur by this system.

First, the drug chamber 12 need not be hermetic or compatible with Freon gas. Thus, the housing 10 need not be titanium as in the prior art. Rather, it can be selected from other materials such as plastic and the like which are inert yet, have reduced costs and lower weight vis-a-vis titanium. Second, Freon and the requirement of a Freon fill tube to initially charge the device are also eliminated in this system. The benefits contribute to lower costs and higher system reliability.

The resilient foam member 14 deflects uniformly under the application of hydrostatic pressure. Thus, the foam can be manufactured in any shape to fill all voids and spaces in the housing 10. FIG. 1 in cross section illustrates the member 14 as occupying substantially the entire drug chamber 12. The operation of a similar device by reference to FIGS. 2a and 2b.

Considering FIG. 2a (in which like numerals are used to identify like components), the foam member 14 is illustrated at its initial, pre-set compression pressure as part of implantable infusion pump 48. That is, the system is manufactured with the foam 14 in partial compression and sealed with barrier skin 16. This defines an initial volume 12 for drug storage. As illustrated in FIG. 2a, the device is implanted under the dermal line 50. A syringe 52, filled with drug solution 53 and incorporating plunger 54 and hollow needle 56, penetrates the dermis 50 and septum 20 to enter fluid antechamber 58. The needle 56 abuts against needle stop 60, preventing entry to the drug chamber 12. Antechamber 58 communicates with drug chamber 12 through flow passages 62.

Within housing 10, an outlet conduit 64 permits passage of drug from chamber 12 through porous bacteria filter 66 and orifice flow restrictor 68 which is constructed of rigid body 70 with orifice channel 72. Flow then exits from orifice 72 barbed connector 74 and flexible catheter 28 to the desired site of delivery.

Referring now to FIG. 2b, upon depression of the plunger 54 in the direction of the arrow 78, the drug solution 53 fills antechamber 58 and passes via flow passages 62 into the drug chamber 12. When the hydrostatic pressure due to filling reaches the initial compression pressure of the foam 14, the foam 14 begins to deflect on all surfaces, commencing the filling operation. This uniform deflection is illustrated by small arrows 80. As the syringe plunger 54 continues to be depressed, the drug chamber 12 fills with the drug 53 until the syringe 52 is emptied or the foam 14 resists further deflection. The syringe needle 56 may then be retracted and the infusion reservoir 1 is ready for use.

Due to the compression of the foam 14, drug chamber 12 is pressurized to a level above that existing at the exit of delivery catheter 28, forcing drug 53 to be expelled through outlet conduit 64, filter 66 restrictor 68 and barbed connector 74. As drug 53 is discharged from drug chamber 12, the compressed foam 14 returns to its initial shape, filling substantially all of the drug chamber 12 until all drug is exhausted and the foam 14 returns to its preset compression position as illustrated in FIG. 2a. Thus, the system has been emptied and is ready for refill in the manner just discussed.

The foam 14 must, in its manufactured shape, exhibit a pressure/volume performance which is acceptable to the flowrate requirements of the intended pump. That is, it must be designed to induce substantially constant pressure or varying degrees of pressure versus volume as required by the particular application. Additionally, the materials to construct foam 14 or barrier skin 16, must be compatible with a variety of solutions to be infused in the body because they come in direct contact with the drug solution 53. The materials of construction in contact with the drug solution must therefore not adversely affect the drug or, visa-versa must not be altered by the drug itself.

Since the foam is in contact with the drug it must meet U.S.P. Class VI criteria. That is, the material must not elute chemicals which will sensitize the body in any manner. That is, the elutents, if any, must be non-pyrogenic, hemocompatible, non-toxic, non-cytotoxic, etc. The same characteristics must also hold true for the barrier skin 16 material and the housing 10 material. Materials satisfactory for the foam 14 include medical grade silicones and polyurethanes. Materials satisfactory for the barrier skin 16 and housing 10 include fluorocarbons and chlorofluorocarbons such as PVDF ("KYNAR", trade name of the ATOCHEM corporation), CTFE, ECTFE, polysulfones, polyesters such as "MYLAR" (DuPont trade name) and thermoplastic polyesters such as "HYTREL" (DuPont trade name). These materials can also be metallized to produce the required barrier properties using elements such as aluminum or titanium or coated with other gas barriers such as diamond-like carbon coating (DLCC).

Because the system is implanted it must achieve acceptable mechanical performance over time. That is, the foam 14 must have acceptable creep characteristics, stable modulus and a relatively long fatigue life. Both the silicone and polyurethane materials mentioned above exhibit these characteristics. Finally, if a closed cell foam is used in direct contact with drug solutions, the foam must have a relative impermeability of the foam surface and/or cell walls to both gases and vapors so that the pressure/volume characteristics of the foam can be maintained over time.

Figure 3B:
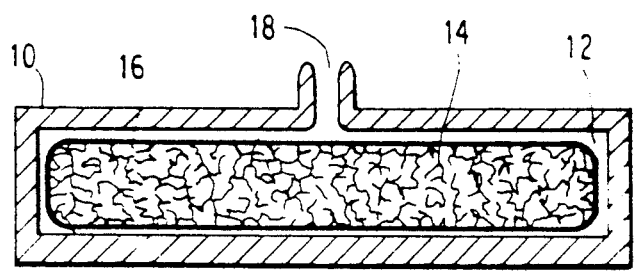

To accomplish these goals, a variety of foam constructions are preferred as illustrated in FIGS. 3a, 3b, 3c, 3d and 3e. Referring now to FIG. 3a, the reservoir 1 may consist of a closed cell foam 14 inside of the rigid housing 10, forming drug chamber 12 in fluid communication with inlet/outlet conduit 18. Depending on the flow characteristics desired, the closed cells of the foam 14 may contain, for example, air at ambient pressure—giving a very high spring rate foam due to the compression of the gas, or vacuum—giving a spring rate characteristic dependent only upon that of the foam material. Alternatively, the foam 14 may be an open cell foam having an impermeable surface skin 16 as shown in FIG. 3b. The skin 16 may be fashioned by fusing the foam's surface e.g., during the foam casting process or through various other types of application methods including dip coating, spraying, shrinkfitting, heat forming or vapor deposition. In addition, various layers of films and/or coatings may be used to produce specific barrier properties. All of these techniques for processing foams and/or films are well known in the art.

Figure 3C:
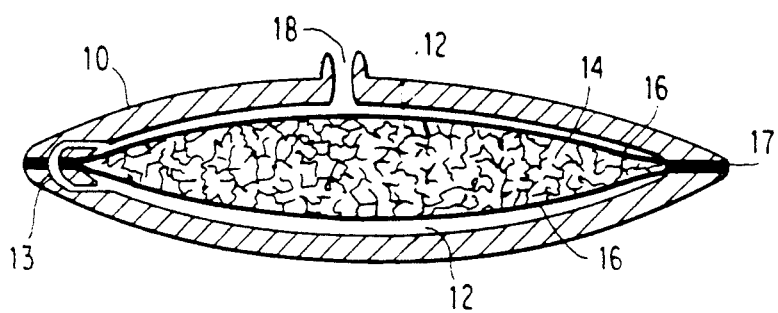

One variation of the open celled foam 14 with skin 16, is displayed in FIG. 3c. Here the skin 16 is formed by two layers of film sealed at the edges to form a hermetic rim 17 "sandwiched" by two opposing sides of the discoid housing 10. To provide fluid continuity between the two sides of the drug chamber 12, a flow passage 13 is created in the walls of the housing 10 and through hermetic rim 17. As in other configurations, the cell volumes within the foam 14 can be filled with gas of a specific type at a specific pressure, or evacuated to give compression characteristics due to the foam material only.

Figure 3D:
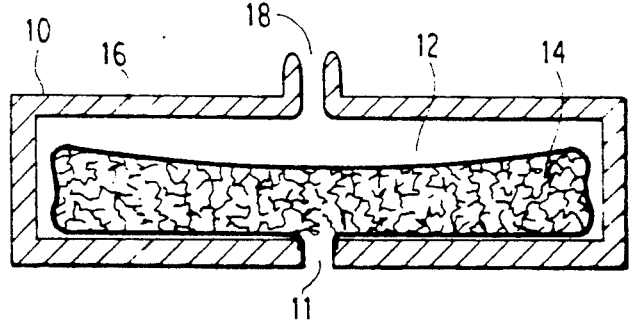

Yet another variation of the reservoir 1 is illustrated in FIG. 3d. Here the foam element 14 is set in a rigid housing 10 that is vented on the foam side via vent hole 11. A barrier skin 16 separates the foam element 14 from the drug chamber 12. The foam element 14 is preferably of the open celled type. Through the vent hole 11 and in combination with the barrier skin 16, the pressure in the drug chamber 12 is made responsive to ambient pressure external to the reservoir 1. The venting technique illustrated in FIG. 3d is useful for maintaining a drug chamber pressure that is independent of changes in ambient pressure, for instance, when a patient with the implanted device travels in a depressurized airplane cabin. By this technique, the device is self compensating for changes in ambient pressure.

Figure 3E:
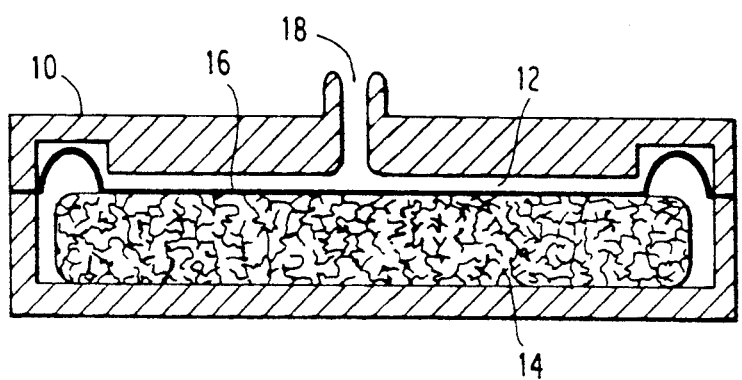

Finally, FIG. 3e represents a reservoir embodiment utilizing a diaphragm as the skin element 16. As before, the foam 14 may be open or closed cell and may be gas charged or evacuated.

Figure 4A:
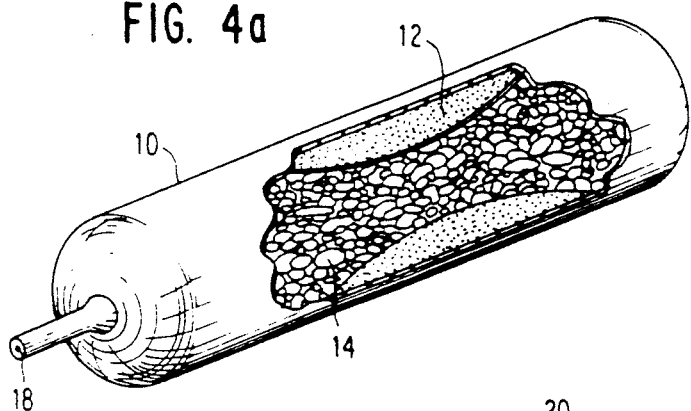
FIGS. 4a, 4b and 4c are three dimensional representations of reservoir configurations constructed in specific "physiologic" shapes.
Figure 4B:
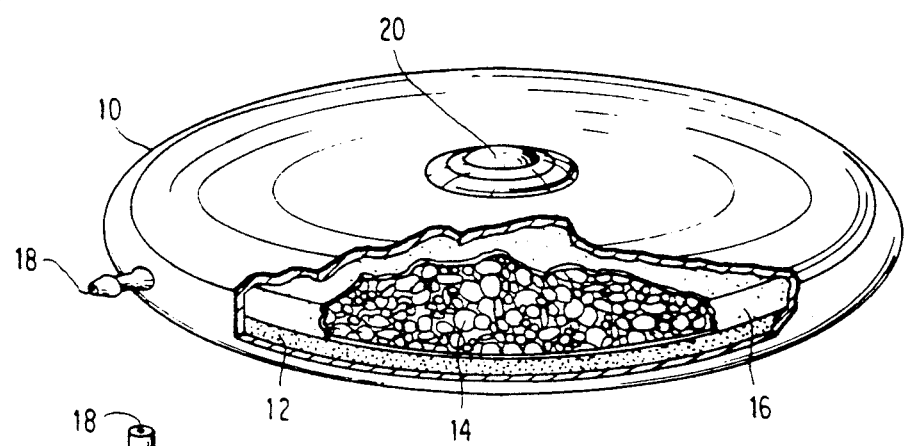
Figure 4C:
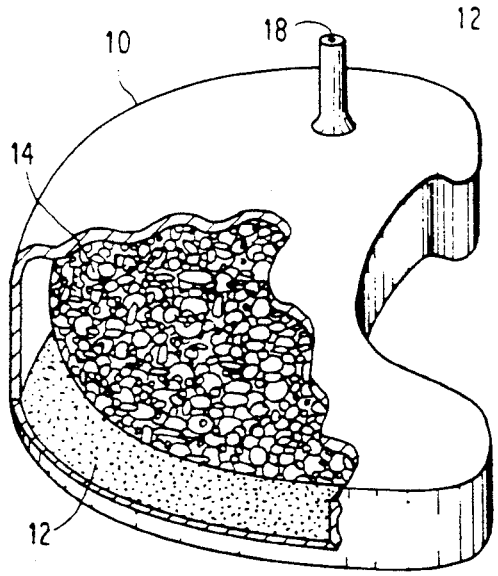

Due to the uniform geometry and deflection of the foam element 14, a variety of reservoir shapes can be designed to accomodate the intended implant location as illustrated in FIGS. 4a, 4b and 4c (where like numbers represent like elements). For instance, FIG. 4a shows a tubular shaped implantable reservoir suited for subcutaneous insertion in the leg or arm. Here only a small incision is required to insert the reservoir and the shape more discreetly and practically conforms to the shape of the limb. FIG. 4b shows a reservoir geometry more amenable to the physiology of a pectoral implant where the reservoir must be large in diameter and thin in height to prevent skin erosion or remain cosmetically appealing. This reservoir is shown with a refill setum 20 as part of the housing 10. The foam element 14 in this reservoir is shown with a barrier skin 16 (illustrated in cut-away cross section). Lastly, FIG. 4c is used to illustrate a non-symmetric housing 10, in this case one that is "kidney shaped". A reservoir of this type may be necessary to conform to a special physiology, for example, around a bone or internal organ or to support a body part or an additional implantable infusion component. All of these shapes are possible because of the inherently uniform deflection of the foam element 14 and the relative ease of forming the foam 14, housing 10 and barrier skin 16 (optional) into a variety of complex geometries. For example, where the device replaces an organ or gland, the shape can replicate the bodily member it replaces to be conformal in the body cavity.

It is therefore apparent that other modifications of this invention can be practiced without departing from the essential scope thereof.

What is claimed is:

1. An implantable infusion system comprising:
   a housing;
   a reservoir in said housing;
   an inlet in said housing for providing access to said reservoir from an external point for charging said reservoir with a fluid to be dispensed;
   an outlet providing fluid communication between said reservoir and a remote location for dispensing said fluid;
   means interposed between said reservoir and said outlet to meter the flow of said fluid; and
   a solid compressible member filling substantially that portion of said reservoir unoccupied by said fluid for providing a force urging said fluid from said reservoir into said outlet by expansion and contracting upon filling said reservoir with fluid.

2. The implantable infusion system of claim 1, wherein said solid compressible member comprises a resilient foam.

3. The implantable infusion system of claim 2, wherein said resilient foam is a closed cell foam.

4. The implantable infusion system of claim 3, wherein said closed cell foam is coated with a solid coating.

5. The implantable infusion system of claim 1, wherein said housing conforms in shape to an implantation site in a body cavity.

6. The implantable infusion system of claim 1, wherein said inlet comprises a penetrable septum.

7. The implantable infusion system of claim 1, wherein said solid compressible member comprises an open cell foam having an impermeable cover thereon.

8. The implantable infusion system of claim 1, wherein said solid compressible member comprises an open cell foam having a separate impermeable cover, and a vent in said housing to expose said solid compressible member to ambient conditions.

9. The implantable infusion system of claim 1 further comprising a diaphragm to compress said solid compressible member in response to fluid pressure during filling.

10. An implantable infusion system comprising:
a hollow housing;
a penetrable septum mounted in said housing for providing access to an interior portion of said housing from an external point for supplying to said housing a fluid to be dispensed;
an outlet catheter establishing fluid communication between said interior portion of said housing and a location for dispensing said fluid; and
a resilient compressible member positioned in said housing and occupying the volume of said interior portion unoccupied by said fluid for providing a force by expansion pressurizing said fluid to expel said fluid from said interior portion into said outlet catheter, said resilient member contacting upon filling said interior portion with fluid.

11. The implantable infusion system of claim 10, wherein said resilient compressible member comprises a resilient foam.

12. The implantable infusion system of claim 11, wherein said resilient foam is a closed cell foam.

13. The implantable infusion system of claim 12 wherein said closed cell foam is coated with a solid coating.

14. The implantable infusion system of claim 10, wherein said resilient compressible member comprises an open cell foam having an impermeable cover thereon.

15. The implantable infusion system of claim 10 further comprising metering means interposed between said housing and said outlet catheter to meter fluid to said outlet catheter.

16. The implantable infusion system of claim 15, wherein said metering means comprises a restriction capillary.

17. The implantable infusion system of claim 15, wherein said metering means comprises an inlet valve, a pressurized volume accumulator and an outlet valve, said inlet and outlet valves operable to alternately fill and discharge said accumulator whereby a metered amount of fluid is delivered to said outlet catheter.

18. The implantable infusion system of claim 15, wherein said metering means comprises a peristaltic pump.

19. The implantable infusion system of claim 10, wherein said housing is shaped to be conformal with a body cavity that is the implantation site.

* * * * *